United States Patent [19]

Norman et al.

[11] Patent Number: 4,495,181

[45] Date of Patent: Jan. 22, 1985

[54] 1,25-DIHYDROXY-24-OXO-VITAMIN $D_3$ AND 1,23,25-TRIHYDROXY-24-OXO-VITAMIN $D_3$

[75] Inventors: Anthony W. Norman, Riverside, Calif.; Eberhard Mayer, Ellwangen, Fed. Rep. of Germany

[73] Assignee: The Regents of the University of California, Berkeley, Calif.

[21] Appl. No.: 538,225

[22] Filed: Oct. 3, 1983

[51] Int. Cl.[3] ............................................. A61K 31/59
[52] U.S. Cl. ................................... 514/167; 260/397.2
[58] Field of Search ..................................... 260/397.2

[56] References Cited

FOREIGN PATENT DOCUMENTS 6061351  5/1981  Japan ................................. 260/397.2

OTHER PUBLICATIONS

Yamada et al., "Jour. Biological Chem.", vol. 258, No. 1, Jan. 10, 1983, pp. 457–463.

Primary Examiner—Elbert L. Roberts
Attorney, Agent, or Firm—Joseph E. Mueth

[57] ABSTRACT

Novel biologically active metabolites of vitamin $D_3$, 1,23,25-trihydroxy-24-oxo-vitamin $D_3(1,23,25(OH)_3$-24-oxo-$D_3$); and 1,25,-Dihydroxy-24-oxo-vitamin $D_3(1,25(OH)_2$-24-oxo-$D_3$). Also the method of preparing these novel metabolites of vitamin $D_3$. The use of these compounds in humans for the treatment of disease states involving calcium homeostatic disorders by the administration of an effective amount of said compounds.

5 Claims, 11 Drawing Figures $1,25(OH)_2$-24-oxo-$D_3$ $1,23,25(OH)_3$-24-oxo-$D_3$

FIG. 6A Flow chart of procedures used for the isolation of $1,23,25(OH)_3$-24-oxo-$D_3$. IPA, isopropyl alcohol.

FIG. 6B Flow chart of procedures used for the isolation of $1,25(OH)_2$-24-oxo-$D_3$. IPA, isopropyl alcohol.

Ultraviolet spectra of 1,24,25-Prime [1,25(OH)$_2$-24-oxo-D$_3$] and Peak X$_b$ [1,23, 25(OH)$_3$-24-oxo-D$_3$]. The compounds were produced by incubation of rat kidney homogenates with 1,24R,25(OH)$_3$D$_3$.

Mass spectra of 1,24,25-Prime (A), 1,25-Prime (B) and 1,25(OH)$_2$-24-oxo-D$_3$ (C).

Mass spectra of Peak $X_b$ (A) and Peak X (B).

FIG. 10 Proton nuclear magnetic resonance spectrum of 1,24,25-Prime. The metabolite was isolated from incubations of 1,24R,25(OH)$_3$D$_3$ with rat kidney homogenates.

Proton nuclear magnetic resonance spectra of Peak $X_b$ (A) and Peak X (B).

Insert: expanded high resolution multiplet of $H_{23}$.

1,25-DIHYDROXY-24-OXO-VITAMIN $D_3$ AND 1,23,25-TRIHYDROXY-24-OXO-VITAMIN $D_3$

This invention was made with Government support under Grant No. AM-09012-17, 18 awarded by the Department of Health and Human Services. The Government has certain rights in this invention.

BACKGROUND OF THE INVENTION

Vitamin D and its metabolites are necessary for the maintenance of calcium homeoslasis. More than 20 metabolites have been discovered to date, varying greatly in biological activity. See, for example, U.S. Pat. No. 3,697,559 which discloses 1,25-dihydroxycholecalciferol which has vitamin D like activity in promoting intestinal calcium absorption.

The novel compounds of this invention are biologically active in terms of both bone calcium mobilization and intestinal calcium absorption and they have been shown to bind to the chick intestinal 1,25(OH)$_2$D$_3$ receptor protein; this receptor protein is believed to mediate the biological responses to these compounds. They are therefore both of clinical importance in treatment of disease states involving calcium homeostasis disorders such as renal osteodystrophy, osteoporosis, hypoparathyroidism, and steroid-induced osteopenia.

The two new vitamin D metabolites of this invention were isolated in pure form from separate incubations of homogenates of chick small intestinal mucosa or rat kidney employing either 1α,25-dihydroxyvitamin D$_3$ [28 µM] or 1α,24R,25-trihydroxy-vitamin D$_3$ as substrate [0.17-1.3 µM]. The newly characterized compounds and the amounts isolated in pure form from separate isolations are respectively: 1α,25-dihydroxy-24-oxo-vitamin D$_3$ [1,25(OH)$_2$-24-oxo-D$_3$], 147 µg (from kidney), 4.2 and 40 µg (from intestine) and 1α,23,25-trihydroxy-24-oxo-vitamin D$_3$ [1,23,25(OH)$_3$-24-oxo-D$_3$] 155 µg (from kidney), 5.9 and 34 µg (from intestine). Their structures were identified after extensive analysis, as well as direct comparison with synthetic 1,25(OH)$_2$-24-oxo-D$_3$. The isolation in pure form and these structural assignments for both compounds correct previous determinations which had been proposed based on impure materials [N. Ohnuma et al. (1982) *J. Biol. Chem.* 257, 5097-5102].

SUMMARY OF THE INVENTION

Briefly, the present invention comprises novel biologically active metabolites of vitamin D$_3$, 1,23,25-trihydroxy-24-oxo-vitamin D$_3$[1,23,25(OH)$_3$-24-oxo-D$_3$] and 1,25-dihydroxy-24-oxo-vitamin D$_3$ [1.25(OH)$_2$-24-oxo-D$_3$].

The present invention also includes the method of preparing the novel compounds 1,25-dihydroxy-24-oxo-vitamin D$_3$ and 1,23,25-trihydroxy-24-oxo-vitamin D$_3$ which comprises incubating the homogenates of chick small intestinal mucosa or rat kidney employing 1,25-dihydroxy vitamin D$_3$ or 1,24,25-trihydroxy-vitamin D$_3$ as substrate, and recovery of said novel compounds.

The invention further comprehends the method comprising the administration of an effective amount of 1,25-dihydroxy-24-oxo-vitamin D$_3$ and/or 1,23,25-trihydroxy-vitamin D$_3$ to humans for the treatment of diseases slates involving calcium homeostasis disorders.

An effective amount of these drugs is the same as known calcium supplements.

It is an object of this invention to provide novel biologically active metabolites of vitamin D$_3$.

It is a further object to provide such compounds in pure form.

A further object of this invention is to prepare novel compounds in pure form by a new route.

These and other objects and advantages of our invention will be apparent from the detailed description which follows.

DESCRIPTION OF THE PREFERRED EMBODIMENTS

Vitamin D$_3$ undergoes a spectrum of metabolic transformations before exerting its biological effects Norman, A. W., Roth, J., and Orci, L. (1982) *Endocrine Rev.* 3, 331-366 and DeLuca, H. F. (1982) *Biochem. Soc. Transactions* 10, 147-158. 1,25(OH)$_2$D$_3$ is recognized as the most active form of the vitamin in terms of enhancing intestinal calcium transport and mobilization of calcium from the skeleton. Besides its activation to 1,25(OH)$_2$D$_3$ by 1α-hydroxylation, 25-OH-D$_3$ can be processed in two different pathways by the kidney: (a) to 25-OH-26,23-lactone D$_3$ via 23S,25(OH)$_2$D$_3$ and 23,25,26(OH)$_3$D$_3$, Ishizuka, S., Ishimoto, S. and Norman, A. W. (1982) *FEBS Lett.* 138, 83-87; or (b) to 23,25(OH)$_2$-24-oxo-D$_3$ via 24R,25(OH)$_2$D$_3$ and 25-OH-24-oxo-D$_3$, Mayer, E., Reddy, G. S., Kruse, J. R., Popjak, G., and Norman, A. W. (1982) *Biochem. Biophys. Res. Commun.* 109, 370-375; Mayer E., Reddy, G. S. Chandraratna, R. A. S., Okamura, W. H., Kruse, J. R., Popjak, G., Bishop, J. E. and Norman, A. W. (1983) *Biochemistry* 22, 1798-1805. Yamada, S., Ohmori, M., Takayama, H., Takasaki, Y. and Suda, T. (1983) *J. Biol. Chem.* 258, 457-463. 1,25(OH)$_2$D$_3$ is known to be metabolized by enzymes located in both the kidney and intestine which are target issues of this steroid hormone, Mayer, E., Williams, G., Kadowaki, S. and Norman, A. W. (1983) In, Kumar, R. (Editor) *Vitamin D. Metabolism: Basic and Clinical Aspects*, Martinus Nijhoff (in press). Its metabolism may lead by hydroxylations at C-24 to 1,24R,25(OH)$_3$D$_3$, Kumar, R., Schnoes, H. K. and DeLuca, H. F. (1978) *J. Biol. Chem.* 253, 3804-3809; Ohnuma, N., Kruse, J. R., Popjak, G., and Norman, A. W. (1982) *J. Biol. Chem.* 257, 5097-5102, at C-26 to 1,25S,26(OH)$_3$D$_3$, Tanaka, Y., Schnoes, H. K., Smith, Tanaka, Y., Schnoes, H. K., Smith, C. M. and DeLuca, H. F. (1981) *Arch. Biochem. Biophy.* 210, 104-109 or by formation of a γ-lactone ring between C-26 and C-23 to 1,25(OH)$_2$D$_3$-26,23-lactone, Ohnuma, N., Bannai, K., Yamaguchi, H., Hashimoto, Y., and Norman, A. W. (1980) *Arch. Biochem. Biophys.* 204, 387-391; Ohnuma, N., and Norman, A. W. (1982) *Arch. Biochem. Biophys.* 213, 139-147. Kumar et al found that 24 h after dosing vitamin D-deficient rats Kumar, R., Harnden, D., and DeLuca, H. F. (1975) *Biochemistry* 15, 2420-2423 or chicks Kumar, R. and DeLuca, H. F. (1976) *Biochem. Biophys. Res. Commun.* 69, 197-200 with physiological amounts of 1,25(OH)$_2$-[26,27-$^{14}$C]-D$_3$, between 10 and 20% of the administered carbon-14 could be detected as $^{14}$CO$_2$. These results indicated that 1,25(OH)$_2$D$_3$ was undergoing oxidative cleavage of the side chain. The site of the cleavage reaction appeared to be the intestine or liver, since enterocolectomy prevented this step Kumar, R. and DeLuca, H. F. (1977) *Biochem Biophys Res Commun.* 76, 253-258. Furthermore, it was suggested that the side chain oxidative reaction is not restricted to 1,25(OH)$_2$D$_3$, but may also involve 1,24,25(OH)$_3$D$_3$, *Biochemistry* 15, supra,. In subsequent work, Esvelt et al. reported the presence of a water-soluble metabolite of 1,25(OH)$_2$D$_3$ with a shortened side-chain in rat liver and intestine, which was chemically characterized as 1α-OH-24,25,26,27-tetranor-23-COOH-D$_3$ (calcitroic acid), Esvelt, R. P., Schnoes, H. K., and DeLuca, H. F. (1979) *Biochemistry* 18, 3977-3983. Also, Yamada et al. have shown that 25(OH)-24-oxo-D$_3$ can be 1α- and 23-hydroxylated in vitro by chick kidney homogenates, *J. Biol. Chem.* 258, supra, Recently Ohnuma and Norman reported *Arch. Biochem. Biophys.* 213, supra, that rat small intestinal mucosa homogenates have the enzymatic capability to convert 1,25(OH)$_2$D$_3$ to 1,24R,25(OH)$_3$D$_3$, 1,25(OH)$_2$-26,23-lactone D$_3$ and another metabolite, which was preliminarily designated Peak X. Peak X was found to be the major chloroform soluble metabolite of 1,25(OH)$_2$D$_3$ in rat intestine in vivo Ohnuma, N. and Norman, A. W. (1982) *J. Biol. Chem.* 257 8261-8271. Its production in vitro was markedly increased by predosing the animals with moderate or large doses of 1,25(OH)$_2$D$_3$. *J. Biol. Chem.* 257, supra. Subsequently, Peak X as well as its precursor, which was preliminarily designated 1,25-Prime, were obtained in pure form from in vitro incubations with chick small intestinal mucosa homogenates; their structures were proposed to be 1,25,26(OH)$_3$-23-oxo-D$_3$ and 1,25(OH)$_2$-23-oxo-D$_3$, respectively, *J. Biol. Chem.* 253, supra. In the present invention we have discovered that the further metabolism of 1,24R,25(OH)$_3$D$_3$ by chick small intestinal mocosa and rat kidney in vitro, cause the enzymatic conversion of 1,24,25(OH)$_3$D$_3$ to two further metabolites which are 1,25(OH)$_2$-24-oxo-D$_3$ (also called 1,24,25-Prime) and 1,23,25(OH)$_3$-24-oxo-D$_3$ (also called Xb) based on ultraviolet absorption spectrophotometry, mass spectrometry, proton nuclear magnet resonance spectrometry and specific chemical reactions. It has been found that these two metabolites are actually present in the impure intestinal in vitro metabolites 1,25-Prime and Peak X, through error which were previously proposed to be 1,25-(OH)$_2$-23-oxo-D$_3$ and 1,25,26(OH)$_3$-23-oxo-D$_3$ *J. Biol. Chem.*, 257, supra, Turning to FIGS. 1 to 5:

FIG. 1 Panel A: Mass spectrum, of the tetra-trimethylsilyl derivative of 1,24,25-Prime [1,25(OH)$_2$-24-oxo-D$_3$]. The trimethylsilyl derivative of the borohydride reduction product of 1,24,25-Prime was evaluated by mass spectrometry. The 1,24,25-Prime was isolated from incubations of rat kidney homogenates with 1,24R,25(OH)$_3$D$_3$. Panel B: Mass spectrum of the tetra-trimethylsilyl derivative of Peak X$_b$ [1,23,25(OH)$_3$-24-oxo-D$_3$]. The trimethylsilyl derivative of Peak X$_b$ was evaluated by mass spectrometry. Peak X$_b$ was isolated from incubations of 1,24R,25(OH)$_3$D$_3$ with rat kidney homogenates.

FIG. 3. HPLC profiles of metabolites produced in incubations of rat kidney homogenates (A) and chick intestinal mucosa homogenates (B). Top panels, migration patterns of standard compounds, measured by ultraviolet absorbance. Bottom panels, incubation of homogenates with tritium-labeled 1,25(OH)$_2$D$_3$, 1,24R,25(OH)$_3$D$_3$ or 1,25(OH)$_2$-24-oxo-D$_3$, as indicated. A μPorasil comlumn (0.39×30 cm) was used, eluted with hexane:isopropyl alcohol (555:65, v/v) at a flow rate of 1 ml/min. Data are expressed as dpm×10$^{-3}$ per ml eluate.

FIG. 5. Induction in intestinal mucosa of 1,25(OH)$_2$D$_3$ metabolizing activity, in vitro after an in vivo priming dose of 1,25(OH)$_2$D$_3$. Vitamin D-deficient chicks (3 birds/group) were given an intravenous priming dose of 1,25(OH)$_2$D$_3$ (1.20 nmol/100 g body weight). The animals were killed at the indicated time intervals and individual incubations (5 min) were carried out with small intestinal mucosal homogenates (10% w/v in 0.25 m sucrose) at 37° C. The incubation media contained 50 mM Tris/Cl, pH 7.4, 3.3 mM MgCl$_2$, 16.7 mM L-malate, and 4.5 ml of homogenate with 15 pmol of 1,25(OH)$_2$-[26,27-$^3$H]-D$_3$ (350,000 cpm). The incubations were terminated by the addition of CHCl$_3$:MeOH, 1:2. The lipid extracts of the incubations were applied directly to a HPLC μPorasil column and eluted with isopropyl alcohol:hexane (11:89). The data are presented as the mean±SD of separate time point samples.

The following Examples are presented solely to illustrate the invention.

EXAMPLE I 1,25(OH)$_2$D$_3$, 1,24R,25(OH)$_3$D$_3$ and 1,24S,25(OH)$_3$D$_3$ were supplied by Hoffmann La Roche Co., Nutley, N.J. 1,25(OH)$_2$-24-oxo-D$_3$ was supplied by Teijin Co., Tokyo, Japan. 25-OH-[26,27-$^3$H]-D$_3$ (specific radioactivity: 15 Ci/mmol) was supplied by Amersham/Searle (Chicago, Il.) and converted to 1,25(OH)$_2$-[26,27-$^3$H]-D$_3$ using kidney homogenates from vitamin D deficient chicks Norman, A. W. and Bishop, J. E. (1980) *Methods in Enzymology: Vitamins and Co-I Enzymes*, Vol. 67, 424-426. 1,24R,25-(OH)$_3$-[26,27-$^3$H]-D$_3$, 1,25(OH)$_2$-24-oxo-[26,27,-$^3$H]-D$_3$ and 1,23,25(OH)$_3$-24-oxo-[26,27,-$^3$H]-D$_3$ were prepared enzymatically by using small intestinal mucosa homogenates of 3 week old vitamin D-deficient chicks, which were primed with 20 U 1,25(OH)$_2$D$_3$ intravenously 6 h before sacrifice. Small intestinal mucosa homogenate (10% in 0.25M sucrose, w/v; 1.5 ml) and buffer (3 ml; 50 mM Tris-HCl, pH 7.4, 3.3 mM MgCl$_2$ and 16.7 mM malate, pH 7.4) were incubated with 1,25(OH)$_2$-[26,27-$^3$H]-D$_3$ (28 nM) for 30 min at 37¼ C. Purification of the metabolites produced was performed by HPLC as described below for the first isolation trial of the unlabeled metabolites.

Animals: White Leghorn cockerels obtained on the day of hatch were raised for three weeks on a diet sufficient in vitamin D before a rachitogenic diet was fed Norman, A. W. and Wong, R. G. (1972) *J. Nutr.* 102, 1709-1718. Two months later the first isolation trial was carried out. The chickens used for the third trial were about 8 months old. For the investigation of the metabolic pathway from 1,25(OH)$_2$D$_3$ to 1,23,25(OH)$_3$-24-oxo-D$_3$, the cockerels were raised on a diet deficient in vitamin D, *Arch. Biochem. Biophys.* Mayer et al, supra, for 3-4 weeks before use.

Male albino Wistar rats weighing 250-300 g were kept in hanging wire cages and fed a normal rat chow.

Isolation of the metabolite

First trial

Figure 6A:
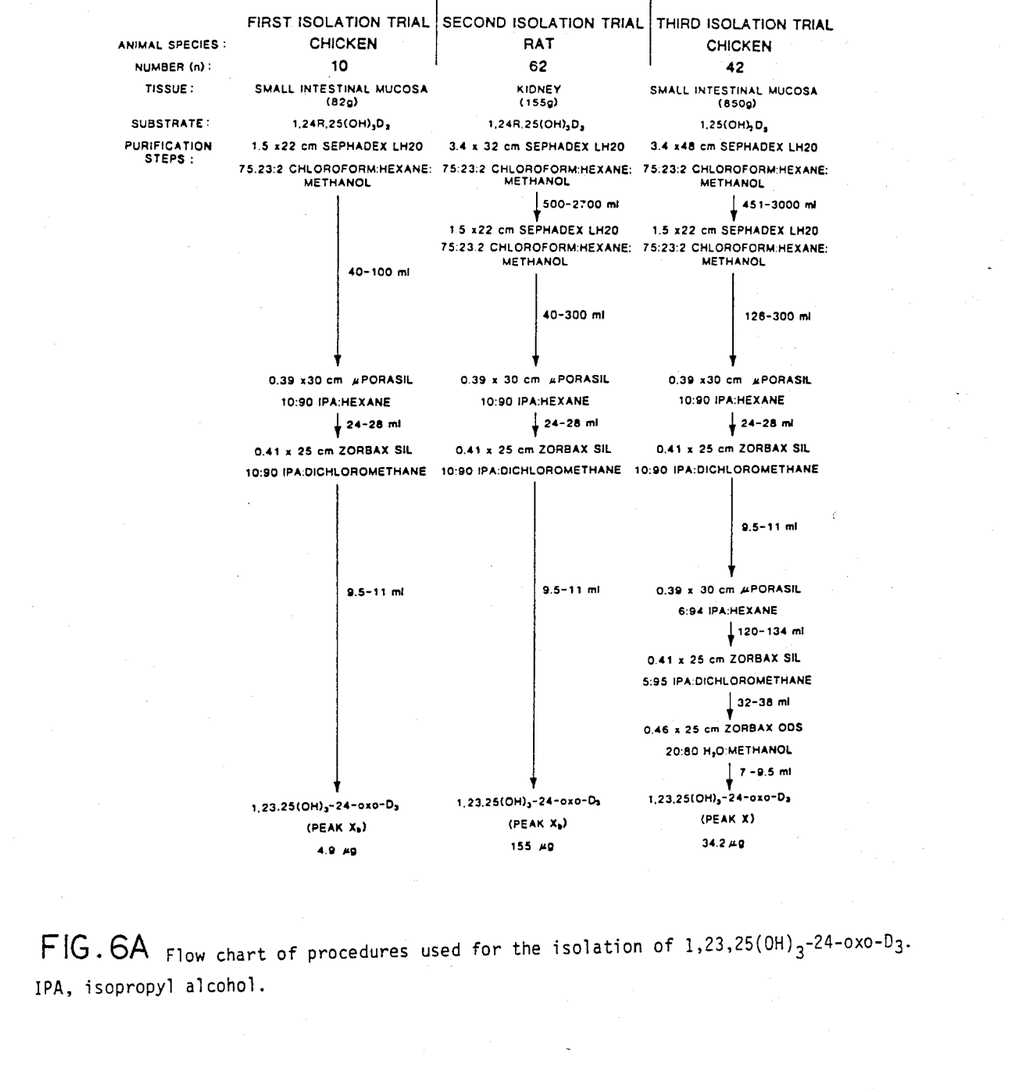
Figure 6B:
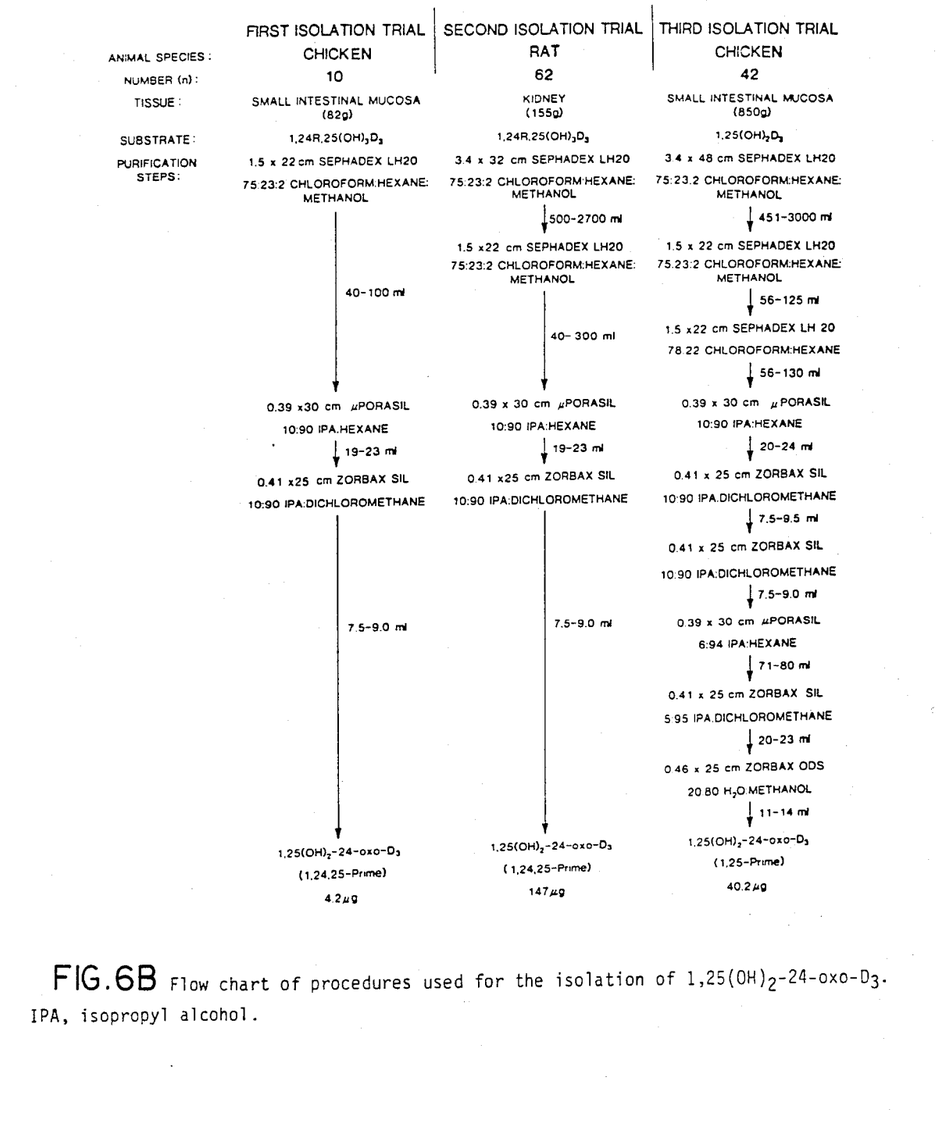

Ten chickens were given 12 nmol/100 g body weight 1,25(OH)$_2$D$_3$ in 0.2 ml 1,2 propanediol:ethanol (1:1, v/v) intravenously. Six hours later the animals were killed by decapitation and the small intestine quickly removed and collected in ice cold saline. A 10% homogenate (w/v) of the scraped mucosa was prepared in 0.25M sucrose. The incubation was carried out at 37° for 60 min in a shaking water bath in 125 ml Erlenmeyer flasks containing 36 ml of 50 mM Tris-HCl (pH 7.4), 3.3 mM $MgCl_2$, 16.7 mM malate (pH 7.4), 14 ml of the homogenate and $1,24R,25(OH)_3D_3$ ($1.7 \times 10^{-7}$M). The reaction was stopped by the addition of 3 volumes of chloroform:methanol, 1:1. The total lipid extracts were evaporated to dryness in vacuo by rotary evaporation, and chromatographed as shown in FIG. 6. The concentrated lipid extracts were divided into 3 equal aliquots and applied to Sephadex LH-20 columns ($1.5 \times 22$ cm, Pharmacia) which were eluted with chloroform:hexane:methanol (75:23:2). The fraction from 40–100 ml was collected, pooled, evaporated to dryness in vacuo, and subjected to HPLC. A $\mu$Porasil column ($0.39 \times 30$ cm, Waters Associates) was equilibrated and eluted with hexane:isopropyl alcohol (90:10, v/v), 2 ml/min. Authentic $1,25(OH)_2D_3$ eluted at 17–19 ml. The UV-absorbing material eluting at 19–23 ml (1,24,25-Prime) and 24–28 ml (Peak $X_b$) was collected separately and further purified by HPLC using a Zorbax SIL column ($0.41 \times 25$ cm, DuPont) eluted with dichloromethane:isopropyl alcohol (90:10, v/v), 0.8 ml/min. 1,24,25-Prime eluted at 7.5–9.0 ml and Peak $X_b$ eluted at 9.5–11 ml. The total yield of the incubations from the mucosa of 10 chickens (82 g mucosa) was 4.2 $\mu$g of 1,24,25-Prime and 4.9 $\mu$g of Peak $X_b$.

Second trial

Sixty-two rats were injected with 4 nmol $1,25(OH)_2D_3$ each in 0.2 ml 1,2-propanediol:ethanol (1:1, v/v) subcutaneously. Six hours later the animals were decapitated and the kidneys removed to ice cold saline. A 10% homogenate (w/v) was prepared in 0.25M sucrose. The incubation flasks contained 36 ml of 50 mM Tris-HCl (pH 7.4) 3.3 mM $MgCl_2$, 16.7 mM succinate (pH 7.4), 14 ml of the homogenates, and 20 $\mu$g $1,24R,25(OH)_3D_3$ in 100 $\mu$l ethanol. After 60 min incubation at 37° C. in a shaking water bath, the reaction mixtures were extracted with 3 volumes of chloroform:methanol (1:1, v/v). The total lipid extracts were evaporated by rotary evaporation and applied to a Sephadex LH-20 column ($3.4 \times 32$ cm), eluted with chloroform:hexane:methanol (75:23:2, v/v). Standard $1,25(OH)_2$-$[^3H]$-$D_3$ eluted from this column at 680–900 ml. The fraction from 500–2700 ml was collected concentrated in vacuo and applied to a second Sephadex LH-20 column ($1.5 \times 22$ cm) eluted with the same solvent system. The fraction from 40–300 ml was collected and subjected to HPLC exactly as in the first isolation trial (see FIG. 6). The incubation of kidneys from 62 rats yielded 147 $\mu$g of 1,24,25-Prime and 155 $\mu$g of Peak $X_b$.

Third trial

Peak X was prepared exactly as described by Ohnuma et al (1982) J. Biol. Chem. 257, 5097–5102, using the small intestinal mucosa from 42 chickens. Additional chromatography steps were required (as outlined in FIG. 6) to purify Peak X from the large amounts of lipids in the chloroform extracts. The incubations using the small intestinal mucosa (850 g) from 42 chickens yielded 40.2 $\mu$g of 1,25-Prime and 34.2 $\mu$g Peak X.

EXAMPLE II

Figure 3A:
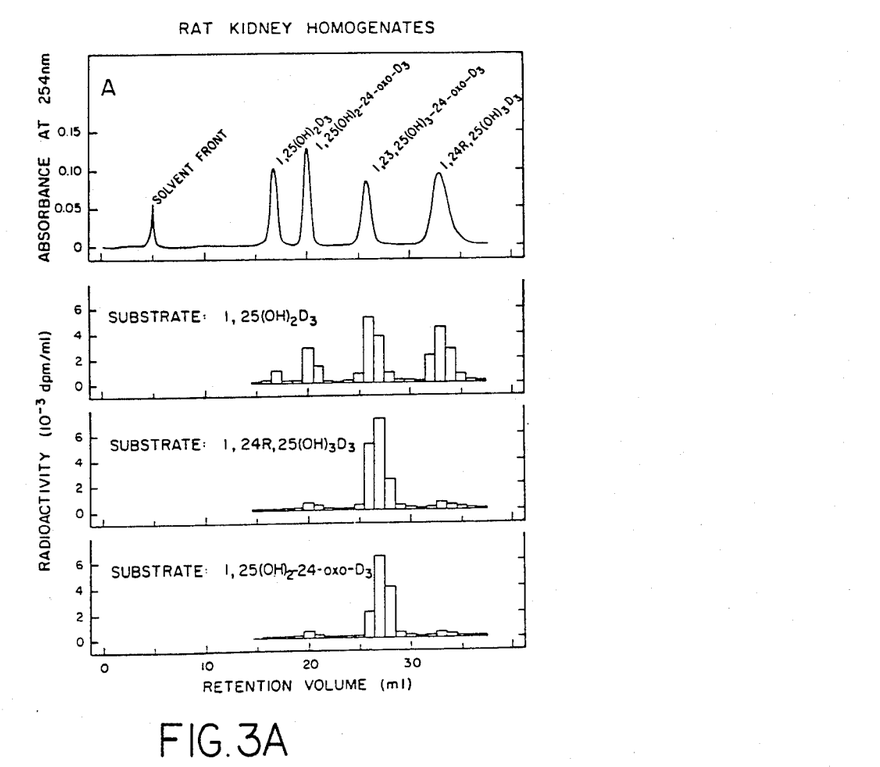
Figure 3B:
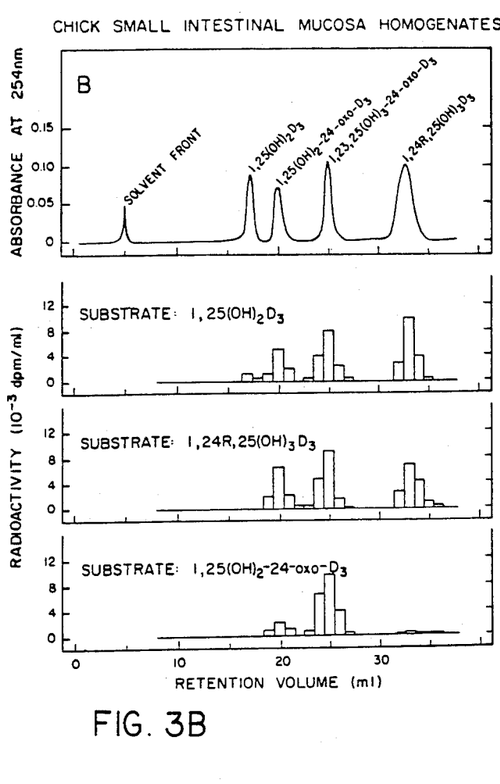

Metabolism of $1,25(OH)_2$-$[^3H]$-$D_3$ to $[^3H]$-Peak X (chicken and $[^3H]$-Peak $X_b$ (rat) $[1,23,25$-$(OH)_3$-$24$-$oxo$-$D_3]$ The metabolic pathway operating in the conversion of $1,25(OH)_2D_3$ to $1,23,25(OH)_3$-$24$-$oxo$-$D_3$ was investigated in both rat kidney and chick small intestinal mucosa. The enzyme activities were induced in vivo by dosing two animals with $1,25(OH)_2D_3$ (1 nmol/100 g body weight) 6 h before sacrifice. A 10% homogenate of each tissue was prepared in 0.25M sucrose. The incubation mixture consisted of 1 ml homogenate, 2 ml of the buffers described above (first isolation trial buffer for chick small intestinal mucosa, second isolation trial buffer for the rat kidney) and 100,000 dpm of either $1,25(OH)_2$-$[26,27$-$^3H]$-$D_3$, $1,24R,25$-$(OH)_3$-$[26,27$-$^3H]$-$D_3$, or $1,25(OH)_2$-$24$-$oxo$-$[26,27$-$^3H]$-$D_3$. The reactions were carried out in duplicate for 15 min at 37° C. in a shaking water bath and were then terminated by the addition of 3 volumes of chloroform:methanol (1:1, v/v). The pooled extracts were subjected to HPLC using a $\mu$Porasil column ($0.39 \times 30$ cm) equilibrated and eluted with hexane:isopropyl alcohol, 90:10 (v/v) at a flow rate of 2 ml/min. The retention volumes of synthetic $1,25(OH)_2D_3$ and $1,24R,25(OH)_3$ and of isolated $1,25(OH)_2$-$24$-$oxo$-$D_3$ and $1,23,25(OH)_3$-$24$-$oxo$-$D_3$ were monitored by absorbance at 254 nm. Fractions (1 ml) were collected and the radioactivity contained was determined by liquid scintillation counting of 500 $\mu$l of each fraction. The radioactive peaks were re-chromatographed on a Zorbax SIL column using dichloromethane:isopropyl alcohol, 90:10 (v/v) as a solvent system (FIG. 3).

Chemical modifications of the metabolites

Borohydride Reduction

Compound (3 $\mu$g) was incubated with 200 $\mu$l ethanol containing 0.1% potassium hydroxide with an excess of $NaBH_4$ for 15 h at room temperature. Then 500 $\mu$l $H_2O$ was added the product was extracted with $3 \times 500$ $\mu$l dichloromethane. After evaporation to dryness under a stream of nitrogen, the sample was purified by HPLC using a Zorbax SIL column ($0.41 \times 25$ cm) which was eluted with dichloromethane:isopropyl alcohol (96:4, v/v) at a flow rate of 2 ml/min.

Trimethylsilylation of the metabolites

The compounds (2 $\mu$g) were dissolved in 100 $\mu$l pyridine and reacted for 60 min at 55° C. with 100 $\mu$l of N,O-bis-(trimethylsilyl)-trifluoroacetamide (BSTFA) containing 1% chlorotrimethyl silane (TMS Cl). After evaporation of the solvent under a stream of nitrogen, the sample was applied to a HPLC $\mu$Porasil column ($0.39 \times 30$ cm) which was eluted with ethylacetate:hexane (2.98, v/v) at a flow rate of 0.5 ml/min. The single ultraviolet absorbing peak generated in each reaction was collected and analyzed by mass spectrometry.

Results

Chemical characterization of the in vitro metabolite Peak $X_b$ obtained from incubations with chick small intestinal mucosa homogenates substrate: $[1,24R,25(OH)_3D_3]$ (first trial)

Figure 7A:
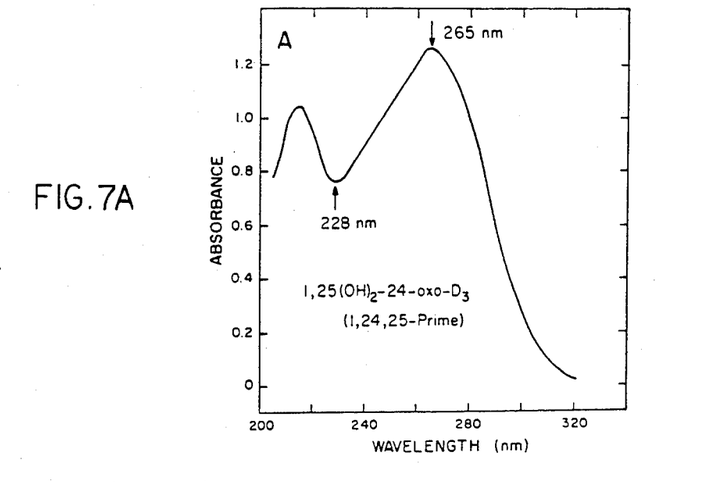
Figure 7B:
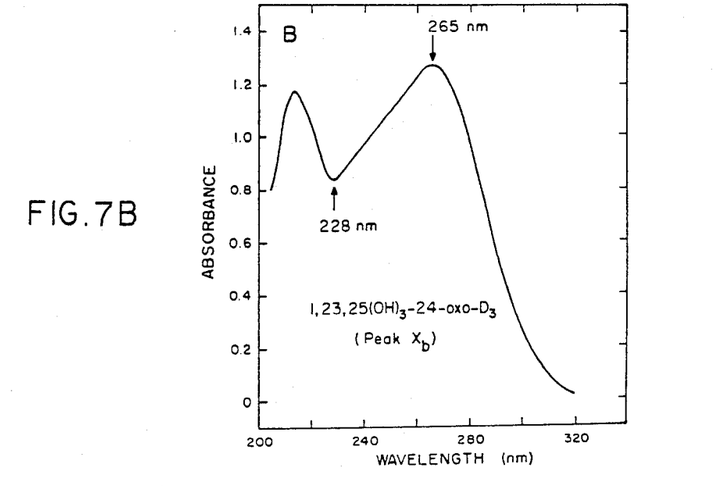

The ultraviolet absorption spectra of 1,24,25-Prime and Peak $X_b$ (FIG. 7) and 1,25-Prime and Peak X (not shown) (taken in 95% ethanol) showed a $\lambda_{max}$ at 265 nm and a $\lambda_{min}$ at 228 nm, characteristic for the vitamin D 5,6-cis-trienechromophore.

Figure 8A:
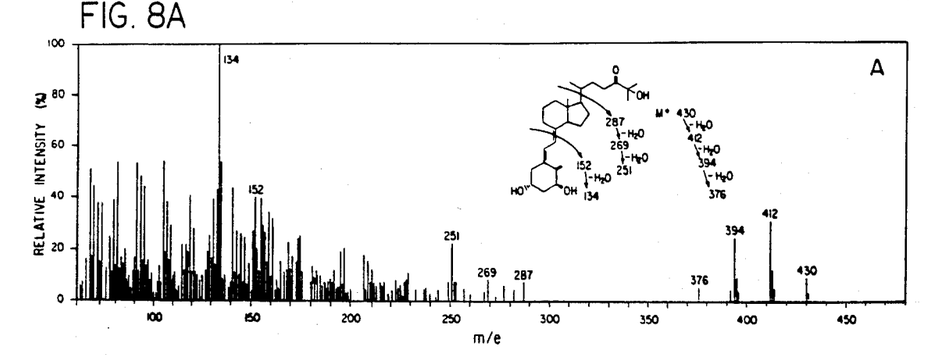

The mass spectrum of the metabolite 1,24,25-Prime is depicted in FIG. 8A. Major ions, relative intensities and structural assignments are as follows: m/e 430, 8, M+; 412, 37 M+-$H_2O$; 394, 26, M+-$2H_2O$; 376, 4, M+$3H_2O$; 287, 6, M+-side chain; 269, 8, 287-$H_2O$; 251, 21, 287-$2H_2O$; 152, 41, (A ring+$C_6$+$C_7$)+; 134, 100, 152-$H_2O$. The apparent molecular ion at m/e 430 suggests the incorporation of one degree of unsaturation (e.g. formation of a cyclic ether, a carbonyl group or an olefinic unsaturation in the molecule) as compared to 1,24R,25(OH)$_3$D$_3$. Characteristic vitamin D cleavage ions at m/e 287, 269, 251, 152 and 134 indicate that the vitamin D nucleus is unaltered and that therefore the modification was introduced in the side chain of the molecule, Okamura, W. H., Hammond, M. L., Jakobs, J. T. C. and van Thuiji, T. (1976) *Tetrahedron Let.* 52, 4807–4814.

Figure 8B:
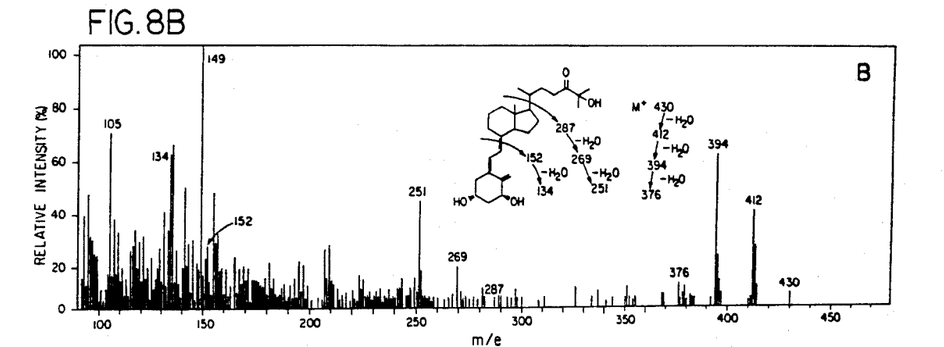

The mass spectrum of 1,25-Prime (third trial) is presented in FIG. 8B. Major ions, relative intensities and structural assignments are as follows: m/e 430, 5, M+; 412, 38, M+-$H_2O$; 394, 59, M+-$2H_2O$; 376, 10, M+-$3H_2O$; 269, 16, M+-side chain; 251, 42, 269-$H_2O$; 152, 24, (A ring+$C_6$+$C_7$)+; 134, 59, 152-$H_2O$. The spectrum of the metabolite contained relatively intense fragments at m/e 149 and 105, which are very probably due to phthalates and related contaminants, Holick, M. F., Kleiner-Bossaller, A., Schnoes, H. K., Kasten, P. M., Boyle, I. T. and DeLuca, H. F. (1973) *J. Biol. Chem.* 248, 6691–6696. Characteristic 1,25(OH)$_2$D$_3$ cleavage ions at m/e 287, 269, 251, 152, and 134 illustrate that the secosteroid nucleus of 1,25(OH)$_2$D$_3$ has remained unchanged and that the metabolic alterations have been introduced on the side chain. The apparent molecular ion at m/e 430 indicates the presence of an additional oxygen atom and one degree of unsaturation in the molecule as compared to 1,25(OH)$_2$D$_3$. The nature and exact location of the unsaturation was elucidated by borohydride reduction of 1,25-Prime. Subsequent HPLC analysis on a Zorbax SIL column (0.41×25 cm) which was eluted with dichloromethane:isopropanol (96:4, v/v) revealed that two compounds were produced which eluted with the same retention volume as synthetic 1,24R,25(OH)$_3$D$_3$ (retention volume: 73 ml) and 1,24S,25(OH)$_3$D$_3$ (retention volume: 78 ml); therefore, the unsaturation in the side chain of 1,25-Prime was established as a ketone group at C-24.

Figure 8C:
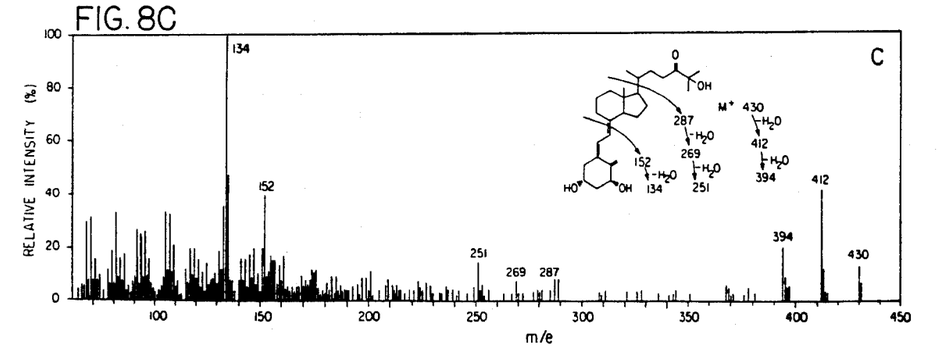

The mass spectrum of synthetic 1,24(OH)$_2$-24-oxo-D$_3$ is shown in FIG. 8C Major ions, relative intensities and structural assignments are as follows: m/e 430, 13 M+; 412, 41, M+-$H_2O$; 394, 20, M+-$2H_2O$; 376, 2, M+-$3H_2O$; 287, 8, M+-side chain; 269, 8, 287-$H_2O$; 251, 16, 287-$2H_2O$; 152, 39 (A ring+$C_6$+$C_7$)+; 134, 100, 152-$H_2O$.

The mass spectra of 1,24,25-Prime and 1,25-Prime are very similar to the spectrum obtained for authentic 1,25(OH)$_2$-24-oxo-D$_3$ and can therefore be readily assigned to a structure 1,25(OH)$_2$-24-oxo-D$_3$.

Figure 9A:
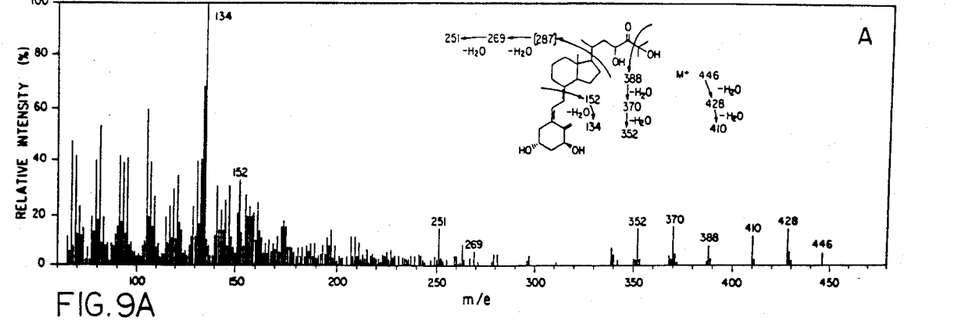

The mass spectrum of Peak X$_b$ (FIG. 9A) showed major ions, relative intensities and structural assignments as follows: m/e 446, 8, M+, 428, 2.7, M+-$H_2O$; 410, 10, M+-$2H_2O$; 388, 6, M+-$C_3H_6O$; 370, 17, 388-$H_2O$; 352, 10, 388-$2H_2O$; 287, 2, M+-side chain; 269, 10, 287-$H_2O$; 251, 10, 287-$2H_2O$; 152, 28 (A ring+$C_6$+$C_7$)+; 134, 100, 152-$H_2O$. The apparent molecular ion at m/e 446 suggests that one oxygen atom and one degree of unsaturation were incorporated into 1,24R,25(OH)$_3$D$_3$, which was the substrate for the enzymatic conversion. The metabolic alterations appeared to be in the side chain of the molecule since the cleavage ions at m/e 287, 269, 251, 152 and 134 indicate that the seco-steroid nucleus was unchanged. The cleavage ions at m/e 228, 370 and 352 are derived from the cleavage between C-24 and C-25 with proton transfer.

Figure 9B:
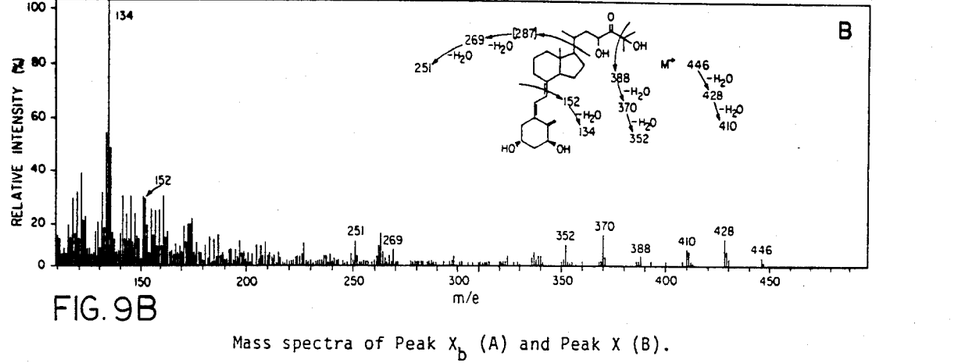

The mass spectrum of Peak X is depicted in FIG. 9B. Major ions relative intensities and structural assignments are as follows: 446, 4, M+; 428, 12, M+-$H_2O$; 410, 6, M+-$2H_2O$; 388, 5, M+-$C_3H_6O$; 370, 12, 388-$H_2O$; 352, 8, 388-$2H_2O$; 269, 6, M+-side chain-$H_2O$; 251, 10, 269-$H_2O$; 153, 26, (A ring+$C_6$+$C_7$)+; 134, 100, 152-$H_2O$. The characteristic fragment ions at m/e 287, 269, 251, 152 and 134 demonstrate that the seco-steroid nucleus was unchanged and that therefore the metabolic alterations must have occurred in the side chain of the molecule. The apparent molecular ion at m/e 446 suggests that two oxygen atoms and one degree of unsaturation were incorporated during metabolism in the 25-hydroxylated side chain. The cleavage ions at m/e 388, 370 and 352 are derived from the cleavage between C-24 and C-25 with proton transfer occurring. Since the major ions in this spectrum were identical to those obtained for Peak X$_b$ (obtained from incubations of 1,24R,25(OH)$_3$D$_3$ with rat kidney homogenates and from incubations of 1,24R,(OH)$_3$D$_3$ with chick small intestinal mucosa homogenates), the structure 1,23,25(OH)$_3$-24-oxo-D$_3$ was assigned for the metabolite Peak X and Peak X$_b$.

Figure 10:
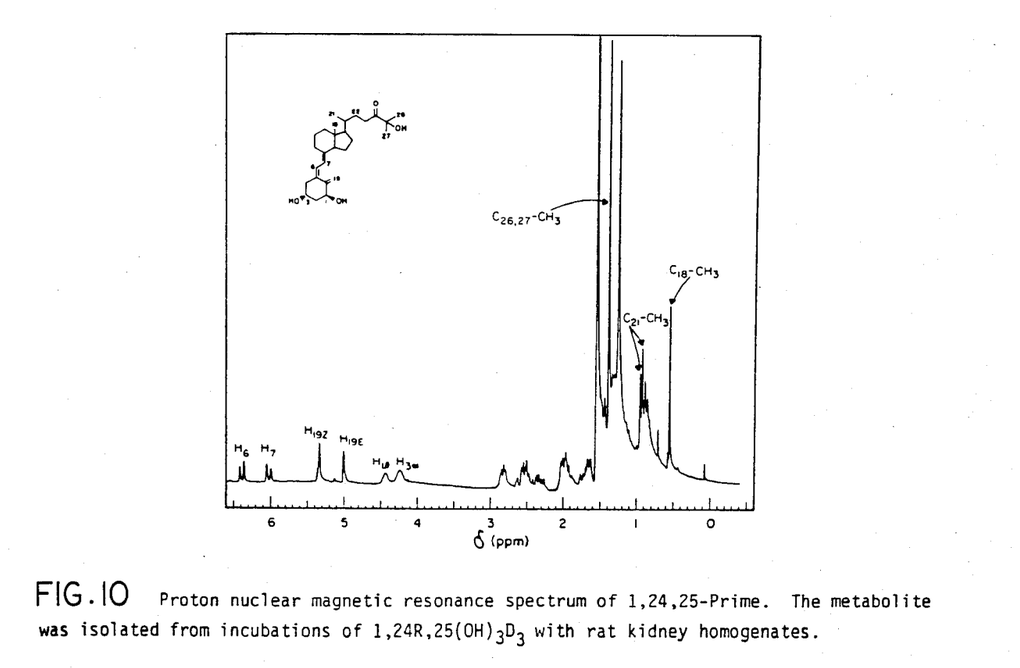

The 200 MHz proton nuclear magnetic resonance spectrum of 1,24,25-Prime is shown in FIG. 10. The presence of an intact 5,6-cis-triene system characteristic of vitamin D was indicated by signals at $\delta$6.39 (H$_6$, d, J=11.2 Hz), 6.03 (H$_7$, d, J=11.2 Hz), 5.34 (H$_{19Z}$, broad s) and 5.01 (H$_{19E}$, broad s). Other characteristic signals were observed at $\delta$4.44 (H$_{1\beta}$, m), 4.24 (H$_{3\alpha}$, m), 1.40 (C$_{26,27}$-CH$_3$, s), 0.94 (C$_{21}$-CH$_3$, d, J=5.86 Hz) and 0.56 (C$_{18}$-CH$_3$, s). The chemical shift ($\delta$1.40) of the C$_{25,27}$-methyl groups in 1,24,25-Prime is of particular significance since these proteons are deshielded by 0.17 ppm relative to the equivalent protons in 1,25(OH)$_2$D$_3$ ($\delta$1.23). This deshielding effect strongly suggests $\beta$-carbonyl substitution at C-24 and is supportive of the assignment of 1,25(OH)$_2$-24-oxo-D$_3$ as the structure for 1,24,25-Prime. Furthermore, a proton-NMR spectrum identical with that obtained for isolated 1,24,25-Prime was obtained for authentic chemically synthesized 1,25(OH)$_2$-24-oxo-D$_3$ (not shown).

The 200 MHz proton-NMR spectrum of synthetic 1,25(OH)$_2$-24-oxo-D$_3$ showed the following signals: $\delta$6.39 (H$_6$, d, J=11.2 Hz), 6.03 (H$_7$, d, J=11.2 Hz), 5.34 (H$_{19Z}$, broad s), 5.01 (H$_{19E}$, broad s), 4.44 (H$_{1\beta}$, m), 4.24 (H$_{3\alpha}$, m), 1.40 (C$_{26,27}$-CH$_3$, s), 0.94 (C$_{21}$-CH$_3$, d, J=5.86 Hz) and 0.56 (C$_{18}$-CH$_3$, s).

Figure 11A:
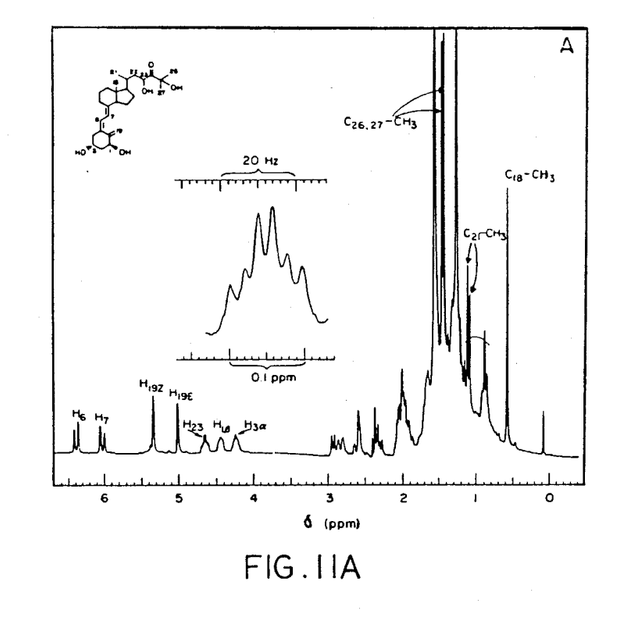

The 200 MHz proton NMR spectrum of Peak X$_b$ (FIG. 11A) clearly indicates the structure of the metabolite to be 1,23,25(OH)$_3$-24-oxo-D$_3$. The spectrum shows signals typical of the 5,6-cis-triene system of vitamin D, Kumar, R. and DeLuca, H. F. (1976) *Biochem. Biophys. Res. Commun.* 69, 197–200 at $\delta$6.39 (H$_6$, d, J+11.2 Hz), 6.02 (H$_7$, d, J=11.2 Hz), 5.34 (H$_{19Z}$, broad s) and 5.01 (H$_{19E}$, broad s). The presence of hydroxyl substitution at C-1 and C-3 was indicated by single proton resonances at $\delta$4.44 (H$_{1\beta}$), m) and 4.23 (H$_{3\alpha}$, m). Other characteristic signals were observed at $\delta$1.10 (C-21 methyl, d, J=6.3 Hz) and 0.57 (C-18 methyl, s). The presence in the side chain of hydroxyl substituents at C-23 and C-25 and of an oxo substituent at C-24 was clearly demonstrated by the following factors: (a) The chemical shifts ($\delta1.46$ and 1.43) of the C-26 and C-27 methyl groups. The C-26,27 methyl signal in 1,25-(OH)$_2$-24-oxo-D$_3$ ($\delta1.40$) is downfield shifted by 0.17 ppm relative to the equivalent signal in 1,25(OH)$_2$D$_3$ ($\delta1.23$) due to the deshielding effect of $\beta$-carbonyl substitution at C-24. Also, a deshielding effect of 0.08 ppm on the C-26,27 methyl groups is observed on C-23 hydroxyl substitution ($\delta1.32$ and 1.28 for 23S,25(OH)$_2$D$_3$ versus $\delta1.22$ for 25-OH-D$_3$. Thus, the signals at $\delta1.46$ and 1.43 in the spectrum of Peak X$_b$ can be assigned to the C-26,27 methyl groups of a 25-OH-D$_3$ side chain which also bears a carbonyl functionality at C-24 and a hydroxyl group at C-23. (b) The presence of a single proton multiplet at $\lambda4.65$ assigned to H$_{23}$. The effect of $\alpha$-carbonyl substitution on a hydroxyl substituted methine is calculated from model compounds to be deshielding by approximately 0.5 ppm. Since the C-23 proton of 23S,25(OH)$_2$D$_3$ appears at $\delta4.1$, the signal at $\delta4.65$ in the spectrum of peak X$_b$ can be reasonably assigned to the C-23 proton of a 23,25(OH)$_2$-24-oxo-D$_3$ side chain. The complexity of the H$_{23}$ signal may be due to virtual coupling of H$_{23}$ with a set of strongly coupled protons including those at C-22 and C-21 or alternatively may be due to coupling with the hydroxyl proton at C-23 under non-exchange conditions in addition to coupling with the adjacent C-22 protons. In summary, the proton NMR spectrum of Peak X$_b$ is completely consistent with the assigned structure of 1,23,25(OH)$_3$-24-oxo-D$_3$.

Figure 11B:
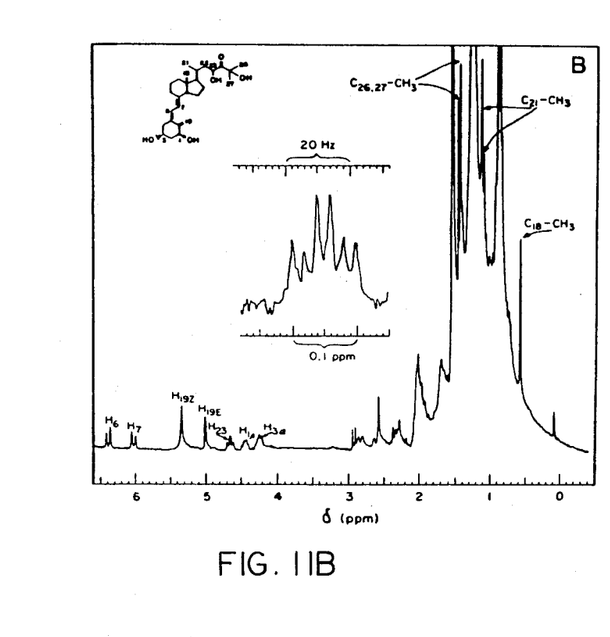

The 200 MHz proton NMR spectrum of Peak X, obtained from incubations of 1,25(OH)$_2$D$_3$ with chicken intestinal mucosa homogenates is shown in FIG. 11B. The signals exhibited and their assignments are as follows: $\delta6.39$ (H$_6$, d. J=11.2 Hz), 6.02 (H$_7$, d, J=11.2 Hz), 5.34 (H$_{19Z}$, broad s), 5.01 (H$_{19E}$, broad s) 4.65 (H$_{23}$, m), 4.44 (H$_{1\beta}$, m), 4.23 (H$_{3\alpha}$, m) 1.46 and 1.43 (C-26,27-methyl, s), 1.10 (C-21 methyl, d, J=6.3 Hz), 0.57 (C-18 methyl, s). The spectrum of Peak X is identical with that obtained for Peak X$_b$ isolated from rat kidney homogenates (FIG. 11A), giving clear evidence for a structure of 1,23,25-(OH)$_3$-24-oxo-D$_3$ for Peak X.

Evidence for the Identity of 1,24,25-Prime, 1,25-Prime and Authentic 1,25(OH)$_2$-24-oxo-D$_3$ by HPLC Chromatography 1,24,25-Prime was isolated from in vitro incubations of 1,24R,25(OH)$_3$D$_3$ with both chick small intestine and rat kidney; 1,25-Prime was obtained from incubations of chick small intestinal mucosa with 1,25(OH)$_2$D$_3$. Firstly, 1 $\mu$g of these three metabolites and of authentic 1,25(OH)$_2$-24-oxo-D$_3$ were chromatographed separately. Then all four compounds were pooled and re-chromatographed. Using a Zorbax SIL-column (0.41×25 cm) and a dichloromethane:isopropyl alcohol (97:3, v/v) solvent system 1,25-Prime, 1,24,25-Prime and 1,25(OH)$_2$-24-oxo-D$_3$ exactly coeluted at 32.4 ml.

Results

Figure 1A:
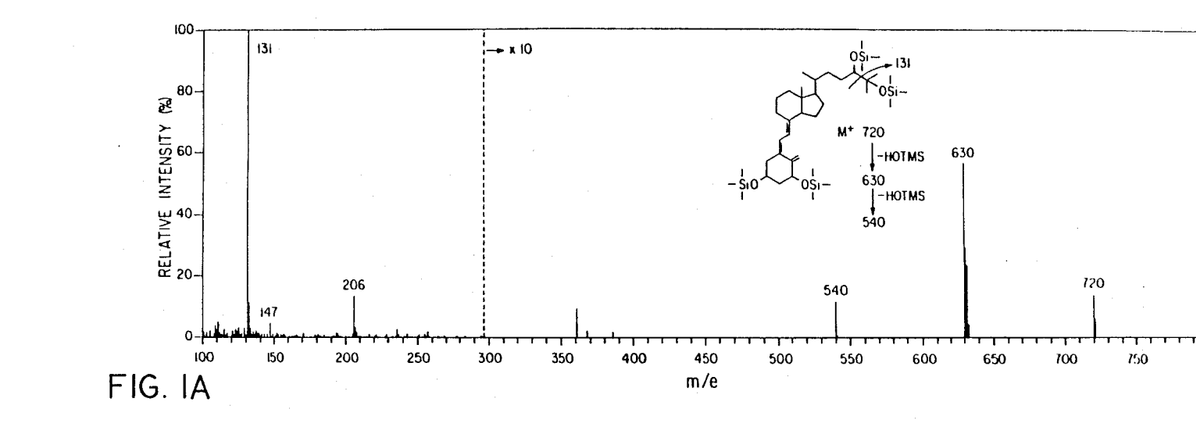

Both new metabolites were isolated in pure form from incubations of rat kidney homogenates with 1,24R,25(OH)$_3$D$_3$. In order to localize the hydroxyl groups in the metabolites, trimethylsilylether derivatives were prepared. First, 1,24,25-Prime was treated with sodium borohydride. Subsequent HPLC analysis on a Zorbax SIL column (0.41×25 cm, solvent system dichloromethane:isopropyl alcohol, 96:4, v/v) showed that two compounds were produced. Two peaks of equal size appeared at retention volumes of 65 ml and 70 ml; these two compounds were co-eluted with authentic chemically synthesized 1,24R,25(OH)$_3$D$_3$ and 1,24S,25(OH)$_3$D$_3$, respectively. These results indicated that the two compounds obtained from the borohydride reduction of 1,24,25-Prime were likely the two possible C24-epimers of 1,24,25(OH)$_3$D$_3$. Subsequent preparation of the trimethylsilylether derivative of the pooled products obtained from the borohydride reduction of 1,24,25-Prime resulted in a compound whose mass spectrum is shown in FIG. 1A. Major ions, relative intensities and structural assignments are as follows: m/e 720, 1.4, M$^+$; 630, 5.7, M$^+$-HOTMS; 540, 1.2, M$^+$-2HOTMS; 206, 13.8, [A ring+C$_6$+C$_7$]$^+$-HOTMS; 147, 5, (CH)$_3$Si-O$^+$=Si(CH$_3$)2; 131, 100, C$_3$H$_6$OTMS$^+$. The apparent molecular ion at m/e 720 suggests that four trimethylsiloxy groups are present in the molecule. The cleavage ion at m/e 131 (base peak) establishes the presence of a siloxy group at C-25 and shows that no further metabolic alterations have occurred at C-26 or C-27. Because this mass spectrum can reasonably be assigned to the tetra-trimethylsilyl derivative of 1,24,25(OH)$_3$D$_3$ (9,19), the structure of this new vitamin D metabolite 1,24,25-Prime can be proposed as 1,25(OH)$_2$-24-oxo-D$_3$.

Figure 1B:
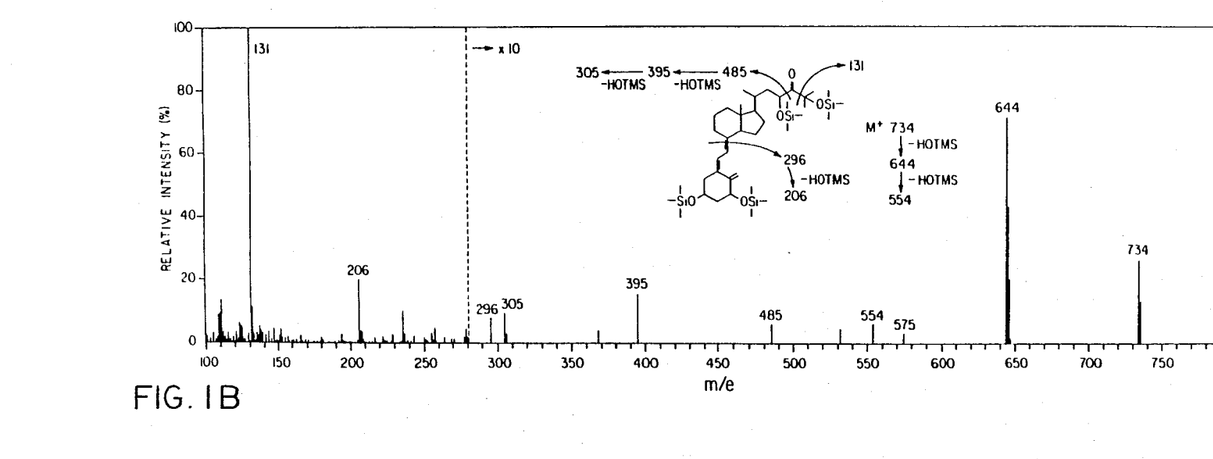

Peak X$_b$ was converted to a tetra-trimethylsilylether derivative. The mass spectrum of this compound is shown in FIG. 1B. Major ions, relative intensities and structural assignments are as follows: m/e 734, 2.7, M$^+$, 644, 7.2, M$^+$-HOTMS; 554, 0.6, M$^+$-2HOTMS; 575, 0.3, M$^+$-C$_4$O$_2$H$_6$TMS; 485, 0.7, 575-HOTMS; 395, 1.6, 575-2HOTMS; 305, 1, 575-3HOTMS; 296, 0.8, (A ring+C$_6$+C$_7$)$^+$; 206, 21, 296-HOTMS: 131, 100, C$_3$H$_6$OTMS$^+$. The apparent molecular ion at m/e 734 demonstrates that four hydroxyl groups are present as trimethylsilylether derivatives in the molecule. The ion at m/e 575 strongly indicates the presence of a hydroxyl group at C-23 and that there are no further alterations below C-23. The cleavage peak at m/e 131 (base peak) establishes the presence of a hydroxyl group at carbon 25 and illustrates that no further modifications at carbon 26 or carbon 27 have occurred. Therefore, the structure of this new vitamin D metabolite is proposed to be 1,23,25(OH)$_3$-24-oxo-D$_3$.

Figure 2:
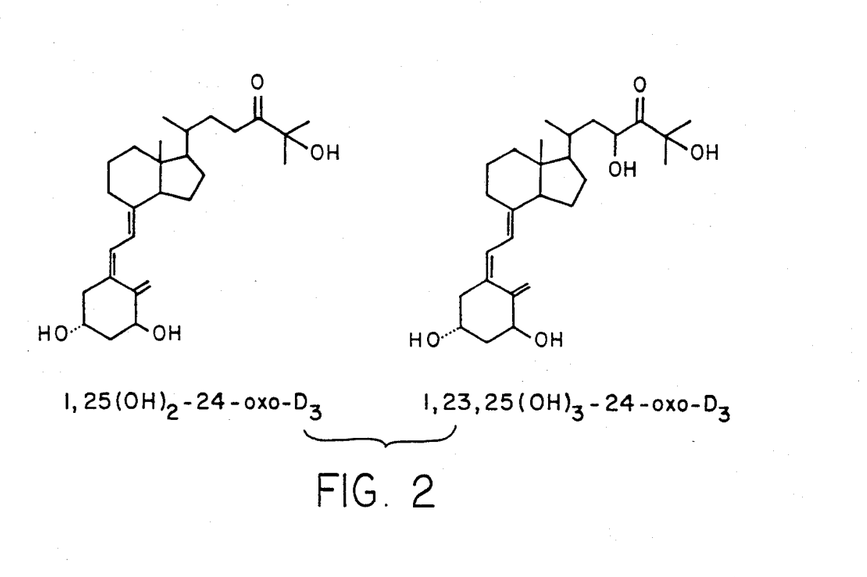
FIG. 2. Structures of 1,25(OH)$_2$-24-oxo-D$_3$ (1,25-Prime, 1,24,25-Prime) and 1,23,25(OH)$_3$-24-oxo-D$_3$ (Peak X, Peak X$_b$).

FIG. 2 shows the structures of 1,24,25 Prime, or 1,25(OH)$_2$-24-oxo-D$_3$ (Panel A), and Peak X$_b$, or 1,23,25(OH)$_3$-24-oxo-D$_3$ (Panel B).

Figure 4:
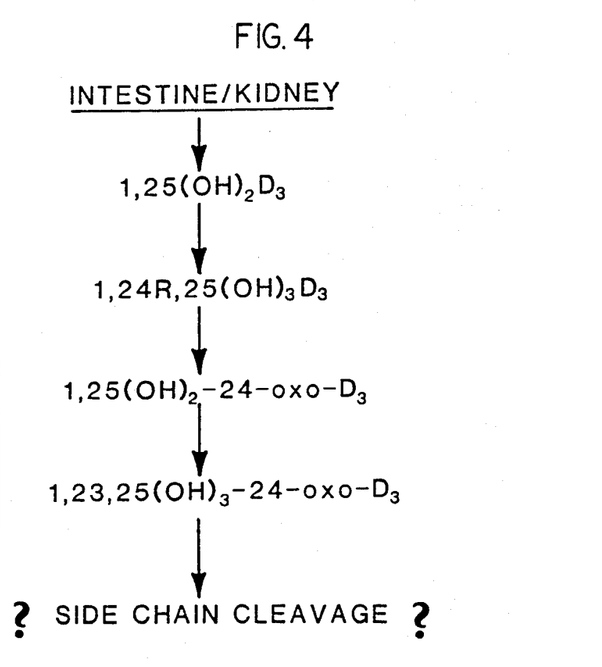
FIG. 4. Proposed pathway of metabolism of 1,25(OH)$_2$D$_3$.

Metabolic Pathway Leading from 1,25(OH)$_2$D$_3$ to 1,23,25(OH)$_3$-24-oxo-D$_3$ in chick small intestinal mucosa in vitro The results of experiments carried out to elucidate the metabolic pathway leading from 1,25(OH)$_2$-[26,27-$^3$H]-D$_3$ to 1,23,25(OH)$_3$-[26,27-$^3$H]-24-oxo-D$_3$ are depicted in FIG. 3. Using kidney homogenates of vitamin D replete rats primed with 1,25(OH)$_2$D$_3$ (FIG. 3A) or small intestinal mucosa homogenates of vitamin D-depleted chicks (FIG. 3B) which were primed with 1,25(OH)$_2$D$_3$, we found that when 1,25(OH)$_2$-[26,27-$^3$H]-D$_3$ was used as a substrate, three further metabolites were produced. These were identified by cochromatography on HPLC with unlabeled material as 1,24R,25(OH)$_3$-[26,27-$^3$H]-D$_3$, 1,25(OH)$_2$-[26,27-$^3$H]-24-oxo-D$_3$ and 1,23,25(OH)$_3$-[26,27-$^3$H]-24-oxo-D$_3$. Furthermore, since 1,25(OH)$_2$-[26,27-$^3$H]-24-oxo-D$_3$ and 1,23,25(OH)$_3$-[26,27-$^3$H]-24-oxo-D$_3$ were also generated in the incubations with 1,24R,25(OH)$_3$-[26,27-$^3$H]-D$_3$ as substrate, it became clear that 1,24R,25(OH)$_3$D$_3$ is an intermediate in their in vitro formation. Incubation of 1,25(OH)$_2$-[26,27-$^3$H]-24-oxo-D$_3$ with the homogenates resulted in the production of 1,23,25(OH)$_3$-[26,27-$^3$H]-24-oxo-D$_3$ and trace amounts of 1,24R,25(OH)$_3$-[26,27-$^3$H]-D$_3$. In summary, the results described above present conclusive evidence for a metabolic pathway present in rat kidney and in chick small intestine leading from 1,25(OH)$_2$D$_3$ to 1,24R,25(OH)$_3$D$_3$ to 1,25(OH)$_2$-24-oxo-D$_3$ to 1,23,25-(OH)$_3$-24-oxo-D$_3$ (FIG. 4).

Figure 5:
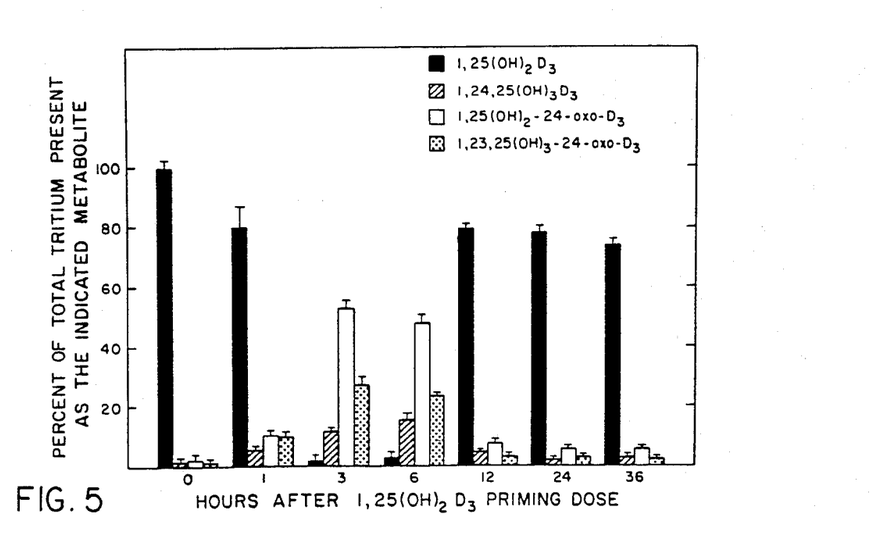

FIG. 5 presents evidence supporting the physiological relevance of the further metabolism of 1,25(OH)$_2$D$_3$ in the chick intestine. The time course of the 1α-OH-seco-steroid metabolism after priming the animals with 1,25(OH)$_2$D$_3$ was studied. The results indicate that by 3-6 h after the priming dose of 1,25(OH)$_2$D$_3$ the 1,25(OH)$_2$D$_3$ metabolizing activity has reached a maximum; this activity then decays away to baseline levels by 12 h. These results suggest the presence of a C-24 oxidation pathway for 1,25(OH)$_2$D$_3$ present in the intestine as well as the kidney.

This report describes the in vitro production, isolation, and chemical characterization of 1,25(OH)$_2$-24-oxo-D$_3$ and 1,23,25(OH)$_3$-24-oxo-D$_3$ which were obtained from incubations of rat kidney homogenates and chicken small intestinal homogenates. The structural assignments are based on ultraviolet absorption spectroscopy, mass spectrometry, and proton nuclear magnetic resonance spectrometry. After induction of the enzymes(s) by priming the animals with high doses of 1,25(OH)$_2$D$_3$ [FIG. 5 and (17)], 1,23,25(OH)$_3$-24-oxo-D$_3$ was produced from 1,25(OH)$_2$D$_3$, 1,24R,25(OH)$_3$D$_3$, and from 1,25(OH)$_2$-24-oxo-D$_3$ by incubation with chick small intestinal mucosa homogenates and rat kidney homogenates. 1,25(OH)$_2$-24-oxo-D$_3$ and 1,23,25(OH)$_3$-24-oxo-D$_3$ are in vitro metabolites of 1,25(OH)$_2$D$_3$, produced enzymatically by sequential hydroxylation at C-24, oxidation of the C-24 hydroxyl group, and hydroxylation at C-23.

The metabolites produced by incubation of 1,25(OH)$_2$D$_3$ with chick small intestinal homogenate (1,25-Prime and Peak X) are 1,25(OH)$_2$-24-oxo-D$_3$ and 1,23,25(OH)$_3$-24-oxo-D$_3$, and not 1,25(OH)$_2$-23-oxo-D$_3$ and 1,25,26(OH)$_3$-23-oxo-D$_3$ as previously proposed, Ohnuma, N. et al (1982) *J. Biol. Chem.* 257, 5097–5102.

The purification of 1,25(OH)$_2$-24-oxo-D$_3$ and 1,23,25(OH)$_3$-24-oxo-D$_3$ from incubations of homogenates of 62 rat kidneys required two Sephadex LH-20 chromatography steps and two HPLC steps, to yield 147 μg (1,24,25-Prime) and 155 μg (Peak X$_b$) respectively. These incubation products comigrated in two HPLC systems with previously isolated metabolites, 1,25-Prime and Peak X respectively, Ohnuma, N., et al (1982) J. Biol. Chem. 257, 5097–5102, which were generated from 1,25(OH)$_2$D$_3$ by incubation with chick small intestinal mucosa hemogenates. The higher lipid content of the intestinal mucosa homogenates necessitated additional HPLC purification steps to obtain 40.2 μg of 1,25-Prime and 34.2 μg of Peak X from the intestinal homogenates of 42 chickens. Structural analyses of 1,25-Prime and 1,24,25-Prime by mass spectrometry and proton NMR spectrometry and the chemical reduction of 1,24,25-Prime to 1,24,25(OH)$_3$D$_3$ clearly showed that both products are identical to 1,25(OH)$_2$-24-oxo-D$_3$. Similar analyses of Peak X and Peak X$_b$ showed that these metabolites are 1,23,25(OH)$_3$-24-oxo-D$_3$.

While the physiological significance, in vivo, of 1,25(OH)$_2$-24-oxo-D$_3$ and 1,23,25(OH)$_3$-24-oxo-D$_3$ are not yet known with certainty it seems likely that they represent a means of further metabolism and inactivation of the highly biologically active 1,25(OH)$_2$D$_3$. As shown in FIG. 5, priming doses of 1,25(OH)$_2$D$_3$ given in vivo result in the rapid induction by 3-6 h of the enzymes necessary for the further metabolism of 1,25(OH)$_2$D$_3$. It also seems significant that this enzymatic activity is present in target tissues; both the intestine and kidney have been shown to contain receptors for 1,25(OH)$_2$D$_3$ and to produce biological responses including induction of a calcium binding protein (CaBP), Norman A. W., Roth, J., and Orci, L. (1982) *Endocrine Rev.* 3, 331–366 and Mayer, E., Williams, G. Kadowaki, S. and Norman A. W. (1983) In, Kumar, R. (Editor) *Vitamin D Metabolism: Basic and Clinical Aspects,* Martinus Nijhoff (in press). Thus, it is possible to propose that the C-24 oxidation pathway which involves the sequential 24-hydroxylation, 24-hydroxyl oxidation and 23-hydroxylation of 1,25(OH)$_2$D$_3$ is an important physiological means of controlling the concentration of hormone and thus the biological response in the target issue.

The biological activity of the vitamin D$_3$ metabolites, as measured by intestinal calcium absorption and bone calcium mobilization in vitamin D-deficient chicks, decreases in the order 1,25(OH)$_2$D$_3$ > 1,24R,25-(OH)$_3$D$_3$ > 1,25(OH)$_2$-24-oxo-D$_3$ > 1,23,25(OH)$_3$-24-oxo-D$_3$. These results also can be interpreted as supportive evidence for the biological significance of the proposed C-24 pathway of the side chain metabolism of 1,25(OH)$_2$D$_3$, leading perhaps to calcitroic acid, Esvelt, R. P., Schnoes, H. K., and DeLuca, H. F. (1979) *Biochemistry* 18, 3977–3983. Both 1,25(OH)$_2$-24-oxo-D$_3$ and 1,23,25(OH)$_3$-24-oxo-D$_3$ were also found to bind to the chick intestinal 1,25(OH)$_2$D$_3$ receptor, being 98% and 28%, respectively, as effective as 1,25(OH)$_2$D$_3$ in competition for ligand binding, Mayer, E., Bishop, J. E., Ohnuma, N. and Norman, A. W., (1983) *Arch.Biochem.-Biophys.* 224, 671–676. This result is indicative of a possible biological significance of these metabolites in the regulation of calcium and/or phosphorus homeostasis.

Two pathways are now apparent for the metabolism of 1,25(OH)$_2$D$_3$ in its target tissues intestine and kidney. One pathway leads to 1,25(OH)$_2$D$_3$-26,23-lactone, Ohnuma, N., Bannai, K., Yamaguchi, H., Hashimoto, Y., and Norman, A. W. (1980) *Arch. Biochem, Biophys.* 204, 387–391 and Ohnuma, N., and Norman, A. W. (1982) *Arch. Biochem. Biophys.* 213, 139–147, whose biological function is as yet unknown. By analogy to the metabolism of 25-OH-D$_3$ to 25-OH-D$_3$-26,23-lactone, Mayer, E., Reddy, G. S., Kruse, J. R., Popjak, G., and Norman, A. W. (1982) *Biochem. Biophys. Res. Commun.* 109, 370–375 and Napoli, J. L. Pramanik, B. C., Partridge, J. J., Uskokovic, M. R. and Horst, R. L. (1982) *J. Biol. Chem.* 257, 9634–9639, C-23 hydroxylation of 1,25(OH)$_2$D$_3$ followed by C-26 hydroxylation and oxidation to the C-26 acid can be postulated as intermediate steps. The second pathway, proposed here, leads from 1,25(OH)$_2$D$_3$ by C-24 hydroxylation to 1,24R,25(OH)$_3$D$_3$, Kumar, R., Schnoes, H. K. and DeLuca, H. F. (1978) *J. Biol. Chem.* 253, 3804–3809 and Ohnuma, N. and Norman, A. W. (1982) *J. Biol. Chem.* 257, 8261–8271, followed by oxidation of the C-24-hydroxyl group to yield 1,25(OH)$_2$-24-oxo-D$_3$ and subsequent C-23 hydroxylation to give 1,23,25(OH)$_3$-24-oxo-D$_3$. Both pathways may lead through side chain cleavage to the currently accepted final inactivation product of $1,25(OH)_2D_3$, $1\alpha$-OH-24,25,26,27-tetranor-23-COOH-$D_3$ (calcitroic acid) Esvelt, R. P., Schnoes, H. K., and DeLuca, H. F. (1979) *Biochemistry* 18, 3977–3983.

Having fully described the invention it is intended that it be limited only by the lawful scope of the appended claims.

We claim:

1. The method of preparing the novel compounds 1,25-dihydroxy-24-oxo-vitamin $D_3$ and 1,23,25-trihydroxy-24-oxo-vitamin $D_3$ which comprises incubating the homogenates of chick small intestinal mucosa or rat kidney employing 1,25-dihydroxy vitamin $D_3$ or 1,24,25-trihydroxy-vitamin $D_3$ as substrate, and recovering said novel compounds.

2. The method of preparing 1,25-dihydroxy-24-oxo-vitamin $D_3$ which comprises incubating the homogenates of chick small intestinal mucosa or rat kidney employing 1,25-dihydroxy vitamin $D_3$, and recovering said compound.

3. The method of preparing 1,23,25-trihydroxy-24-oxo-vitamin $D_3$ which comprises incubating the homogenates of which small intestinal mucosa or rat kidney employing 1,24,25-trihydroxy vitamin $D_3$ as substrate, and recovering said compound.

4. The novel biologically active metabolite of vitamin $D_3$, 1,23,25-trihydroxy-24-oxo-vitamin $D_3$.

5. The method comprising the administration of an effective amount of 1,23,25-trihydroxy-24-oxo-vitamin $D_3$ to humans for the treatment of disease states involving calcium homeostatis disorders.

* * * * *